US012569192B2

(12) United States Patent
Higuchi et al.

(10) Patent No.: US 12,569,192 B2
(45) Date of Patent: Mar. 10, 2026

(54) ANALYSIS DEVICE

(71) Applicant: NEC Corporation, Tokyo (JP)

(72) Inventors: Masao Higuchi, Tokyo (JP); Mitsuru Noma, Tokyo (JP); Reishi Kondo, Tokyo (JP); Yumi Arai, Tokyo (JP)

(73) Assignee: NEC CORPORATION, Tokyo (JP)

( * ) Notice: Subject to any disclaimer, the term of this patent is extended or adjusted under 35 U.S.C. 154(b) by 423 days.

(21) Appl. No.: 18/021,017

(22) PCT Filed: Aug. 25, 2020

(86) PCT No.: PCT/JP2020/032059
§ 371 (c)(1),
(2) Date: Feb. 13, 2023

(87) PCT Pub. No.: WO2022/044131
PCT Pub. Date: Mar. 3, 2022

(65) Prior Publication Data
US 2023/0293103 A1 Sep. 21, 2023

(51) Int. Cl.
*A61B 5/00* (2006.01)
*A61B 7/00* (2006.01)
(Continued)

(52) U.S. Cl.
CPC ............ *A61B 5/4842* (2013.01); *A61B 7/003* (2013.01); *G16H 15/00* (2018.01); *G16H 20/10* (2018.01); *G16H 50/30* (2018.01)

(58) Field of Classification Search
CPC ....... A61B 5/4842; A61B 7/003; A61B 5/021; A61B 5/14551; A61B 5/08; A61B 7/00;
(Continued)

(56) References Cited

U.S. PATENT DOCUMENTS 6,699,204 B1 3/2004 Kehyayan et al.
2002/0085724 A1 * 7/2002 Grasfield ............... H04M 11/06
381/67
(Continued)

FOREIGN PATENT DOCUMENTS

AU 2014237545 A1 * 10/2015 ........... A61B 5/0024
AU 2018244596 A1 * 10/2019 ........... A61B 5/1455
(Continued)

OTHER PUBLICATIONS

JP Office Communication for JP Application No. 2022-544943, mailed on Aug. 27, 2024 with English Translation.
(Continued)

*Primary Examiner* — Jeffrey G. Hoekstra
(74) *Attorney, Agent, or Firm* — Sughrue Mion, PLLC

(57) ABSTRACT

An analysis device includes a detection unit that detects abnormality in lung sounds for each of auscultation positions on the basis of time-series acoustic signals including lung sounds of each of the auscultation positions; a determination unit that determines severity of heart failure of a patient on the basis of a detection result of abnormality in the lung sounds of each of the auscultation positions detected by the detection unit and condition information representing the condition of the patient; and a decision unit that decides an instruction to be output to the patient on the basis of a result of the determination by the determination unit.

11 Claims, 14 Drawing Sheets

(51) Int. Cl.

| | | |
|---|---|---|
| *G16H 15/00* | (2018.01) | |
| *G16H 20/10* | (2018.01) | |
| *G16H 50/30* | (2018.01) | |

(58) Field of Classification Search
CPC .......... A61B 7/04; G16H 15/00; G16H 20/10; G16H 50/30; G16H 40/67; G16H 40/63; G16H 50/20; G16H 50/70
See application file for complete search history.

(56) References Cited

U.S. PATENT DOCUMENTS

| | | | |
|---|---|---|---|
| 2004/0260188 A1* | 12/2004 | Syed ........................ | A61B 7/04 |
| | | | 600/509 |
| 2007/0073168 A1 | 3/2007 | Zhang et al. | |
| 2008/0013747 A1* | 1/2008 | Tran ......................... | A61B 7/04 |
| | | | 381/67 |
| 2013/0237862 A1 | 9/2013 | Song et al. | |
| 2014/0313303 A1 | 10/2014 | Davis et al. | |
| 2016/0302666 A1* | 10/2016 | Shaya .................... | G16H 10/20 |
| 2017/0325779 A1 | 11/2017 | Spina et al. | |
| 2018/0028144 A1* | 2/2018 | Chen ...................... | A61B 5/316 |
| 2018/0110475 A1* | 4/2018 | Shaya .................... | G16H 10/60 |
| 2020/0077892 A1* | 3/2020 | Tran ...................... | A61B 5/6891 |
| 2020/0118164 A1* | 4/2020 | DeFrank ........... | G06Q 30/0269 |

FOREIGN PATENT DOCUMENTS

| | | | | | |
|---|---|---|---|---|---|
| CN | 107545906 A | * | 1/2018 | .............. | A61B 5/08 |
| EP | 3078329 A1 | * | 10/2016 | ........... | G16H 50/30 |
| JP | 2002-538921 A | | 11/2002 | | |
| JP | 2006-259827 A | | 9/2006 | | |
| JP | 2007-190080 A | | 8/2007 | | |
| JP | 2007-190081 A | | 8/2007 | | |
| JP | 2008-113936 A | | 5/2008 | | |
| JP | 4849424 B2 | | 1/2012 | | |
| JP | 2014-004018 A | | 1/2014 | | |
| JP | 2015524678 A | * | 8/2015 | .............. | A61B 7/04 |
| JP | 2017-536905 A | | 12/2017 | | |
| WO | WO-9814116 A2 | * | 4/1998 | .......... | A61B 5/0823 |
| WO | WO-9834542 A2 | * | 8/1998 | .......... | H04M 11/06 |
| WO | 2010/044452 A1 | | 4/2010 | | |

OTHER PUBLICATIONS

International Search Report for PCT Application No. PCT/JP2020/032059, mailed on Nov. 2, 2020.

* cited by examiner

100  ANALYSIS DEVICE

Fig.2

| AUSCULTATION POSITION | LUNG SOUND DATA |
|:---:|:---:|
| 1 | DATA 1 |
| 2 | DATA 2 |
| ⋮ | ⋮ |
| 12 | DATA 12 |

POSTERIOR SIDE OF THE CHEST

ANTERIOR SIDE OF THE CHEST

Fig.5

| AUSCULTATION POSITION | ANALYSIS RESULT |
|---|---|
| 1 | ANALYSIS RESULT 1 |
| 2 | ANALYSIS RESULT 2 |
| ⋮ | ⋮ |
| 12 | ANALYSIS RESULT 12 |

Fig.6

| AUSCULTATION POSITION | (1) | (2) | (3) | (4) | (5) | (6) | (7) | (8) | (9) | (10) | (11) | (12) |
|---|---|---|---|---|---|---|---|---|---|---|---|---|
| SEVERITY 1 | ⋮ | ⋮ | ⋮ | ⋮ | ⋮ | ⋮ | ⋮ | ⋮ | ⋮ | ⋮ | + | + |
| SEVERITY 2 | ⋮ | ⋮ | ⋮ | ⋮ | + | ⋮ + | ⋮ | ⋮ | ⋮ | ⋮ | + | + |
| ⋯ | × × × | • • • | • • • | • • • | × × × | × × × | • • • | • • • | • • • | × × × | × × × | • • • |
| SEVERITY N | + | + | + | + | + | + | + | + | + | + | + | + |

Fig.7

| SEVERITY IDENTIFICATION INFORMATION | SEVERITY |
|---|---|
| xxxx | SEVERITY 1 |
| ⋮ | ⋮ |

Fig.8

| SEVERITY | INSTRUCTION CONTENT |
|---|---|
| SEVERITY 0~2 | NEXT EXAMINATION INSTRUCTION |
| SEVERITY 3~4 | MEDICATION INSTRUCTION |
| SEVERITY 5~N | SEEKING DIAGNOSIS INSTRUCTION |

Fig.9

| CONDITION IDENTIFICATION INFORMATION | CONDITION INFORMATION |
|---|---|
| xxxx | WEIGHT, MEDICATION, ······ |
| ⋮ | ⋮ |

100  ANALYSIS DEVICE

ANALYSIS SYSTEM 200

ANALYSIS DEVICE

This application is a National Stage Entry of PCT/JP2020/032059 filed on Aug. 25, 2020, the contents of all of which are incorporated herein by reference, in their entirety.

TECHNICAL FIELD

The present invention relates to an analysis device, an analysis method, and a storage medium.

BACKGROUND ART

Heart failure is a clinical syndrome in which as a result that cardiac dysfunction, that is, an organic and/or functional dysfunction, occurred in the heart and compensation mechanism of a heart pump function failed, dyspnea, malaise, or an edema appears, which is accompanied by a drop of exercise tolerability. A patient who suffered from heart failure always has a risk of exacerbation even though the patient has been treated and reached remission. When acute exacerbation occurs in the patient due to excessive water or salt intake, forgetting to take medicines, too much exercise, and the like, the patient must be hospitalized again. Therefore, it is important to prevent acute exacerbation by finding heart failure exacerbation of a patient discharged from hospital in an early stage and giving treatment intervention.

One method of diagnosing heart failure is a lung sound examination by auscultation. Such an examination is a method usable for diagnosing health condition of lungs and also heart failure, in a safe and easy manner. However, it is difficult for those other than skilled medical specialists to obtain a detailed and accurate diagnosis result. Therefore, in the rounds by general nurses or caring staff and in the visiting care sites, it is impossible to obtain a detailed diagnosis.

In order to cope with such a problem, a system has been proposed (for example, see Patent Literatures 1 to 4 and 6). The system automatically determines presence or absence of abnormal sounds called adventitious sounds in the lung sounds collected by an electronic stethoscope. Another system has also been proposed (for example, Patent Literature 5). This system is for detecting abnormality by comparing biological sound data of a patient collected by an electronic stethoscope with normal time data and abnormal time data of the patient acquired in advance.

Further, as related art, Patent Literature 7 has been known. Patent Literature 7 discloses a server device including an advice sentence setting means for automatically creating advice information on the basis of a condition on the number of measurement times and an abnormal value range received from a doctor's terminal.

Patent Literature 1: JP 2014-4018 A
Patent Literature 2: JP 2002-538921 A
Patent Literature 3: JP 2017-536905 A
Patent Literature 4: WO 2010/044452 A
Patent Literature 5: JP 2008-113936 A
Patent Literature 6: JP 4849424 B
Patent Literature 7: JP 2006-259827 A
Patent Literature 8: JP 2007-190081 A

SUMMARY

Even if medical examinations using a system as described in Patent Literatures 1 to 6 are put into practice, it is difficult for patients or the like not having professional knowledge to determine appropriate actions based on the examination result. Further, as described in Patent Literature 7, even if advice information is automatically creased not based on the personal condition, it is still difficult to take appropriate actions corresponding to the personal condition.

In view of the above, an object of the present invention is to provide an analysis device, an analysis method, and a storage medium capable of solving a problem that it may be difficult to take appropriate actions.

An analysis device, according to one aspect of the present invention, is configured to include a detection unit that detects abnormality in lung sounds for each of auscultation positions on the basis of time-series acoustic signals including lung sounds of each of the auscultation positions;

a determination unit that determines severity of heart failure of a patient on the basis of a detection result of abnormality in the lung sounds of each of the auscultation positions detected by the detection unit and condition information representing a condition of the patient; and a decision unit that decides an instruction to be output to the patient on the basis of a result of the determination by the determination unit.

An analysis method, according to another aspect of the present invention, is configured to include, by an information processing device:

detecting abnormality in lung sounds for each of auscultation positions on the basis of time-series acoustic signals including lung sounds of each of the auscultation positions;

determining severity of heart failure of a patient on the basis of a detection result of abnormality in the lung sounds of each of the auscultation positions detected and condition information representing a condition of the patient; and deciding an instruction to be output to the patient on the basis of a result of the determination.

A storage medium, according to another aspect of the present invention, is a computer-readable medium storing thereon a program for causing an information processing device to implement:

a detection unit that detects abnormality in lung sounds for each of auscultation positions on the basis of time-series acoustic signals including lung sounds of each of the auscultation positions;

a determination unit that determines severity of heart failure of a patient on the basis of a detection result of abnormality in the lung sounds of each of the auscultation positions detected by the detection unit and condition information representing a condition of the patient; and a decision unit that decides an instruction to be output to the patient on the basis of a result of the determination by the determination unit.

With the configurations described above, the present invention can provide an analysis device, an analysis method, and a storage medium that enable patients to take appropriate actions.

BRIEF DESCRIPTION OF DRAWINGS

FIG. 2 illustrates an example of lung sound data.

FIG. 5 illustrates an example of analysis result information.

FIG. 6 illustrates an example of severity determination information.

FIG. 7 illustrates an example of severity information.

FIG. 8 illustrates an example of instruction decision information.

FIG. 9 illustrates exemplary information included in personal condition information.

EXEMPLARY EMBODIMENTS

First Exemplary Embodiment

Figure 1:
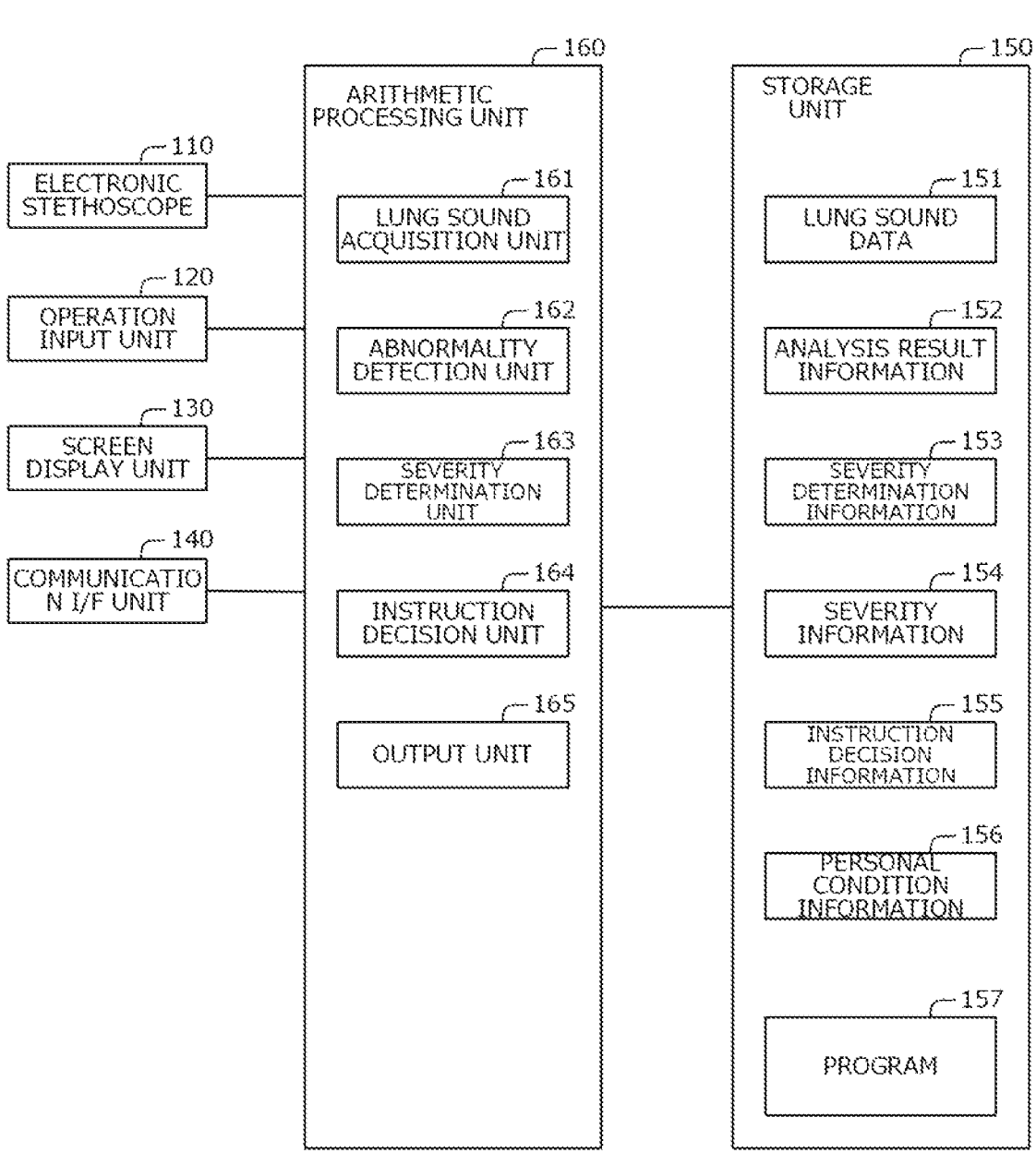
FIG. 1 is a block diagram illustrating an exemplary configuration of an analysis device according to a first exemplary embodiment of the present invention.
Figure 3:
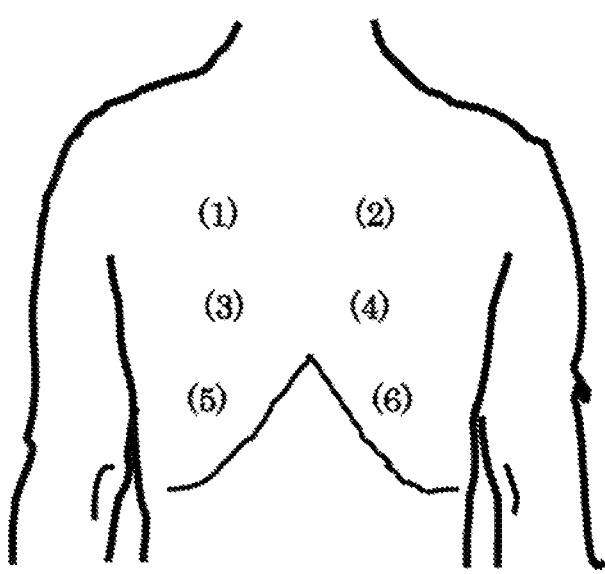
FIG. 3 is a diagram for explaining exemplary auscultation positions.
Figure 4:
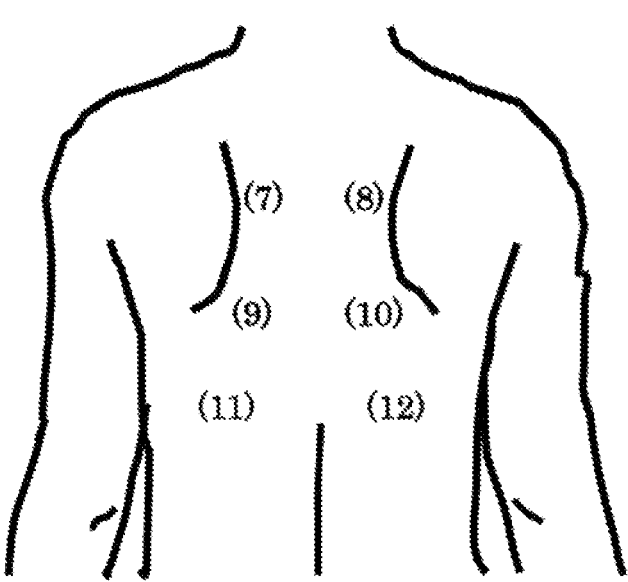
FIG. 4 is a diagram for explaining exemplary auscultation positions.
Figure 10:
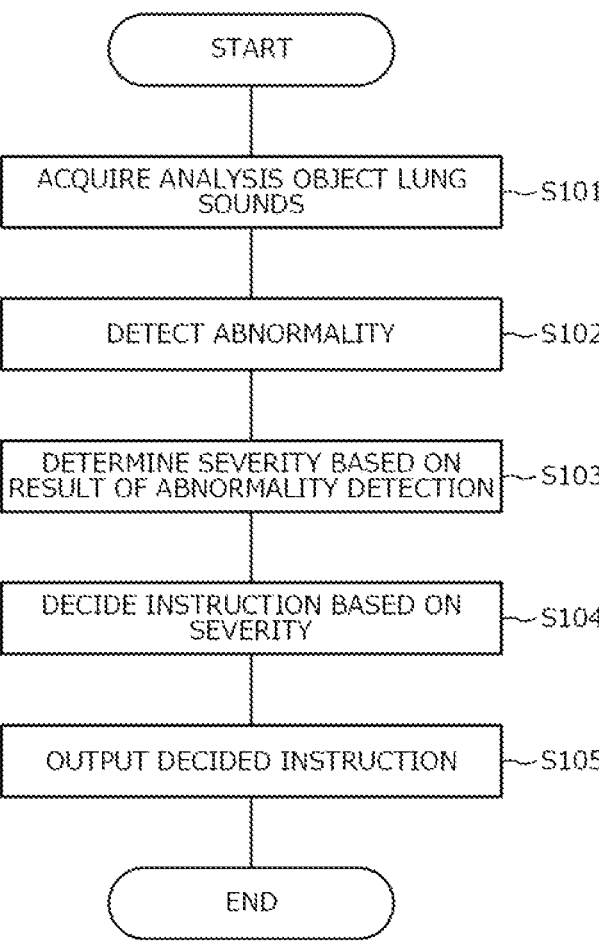
FIG. 10 is a flowchart illustrating an exemplary operation of the analysis device.
Figure 11:
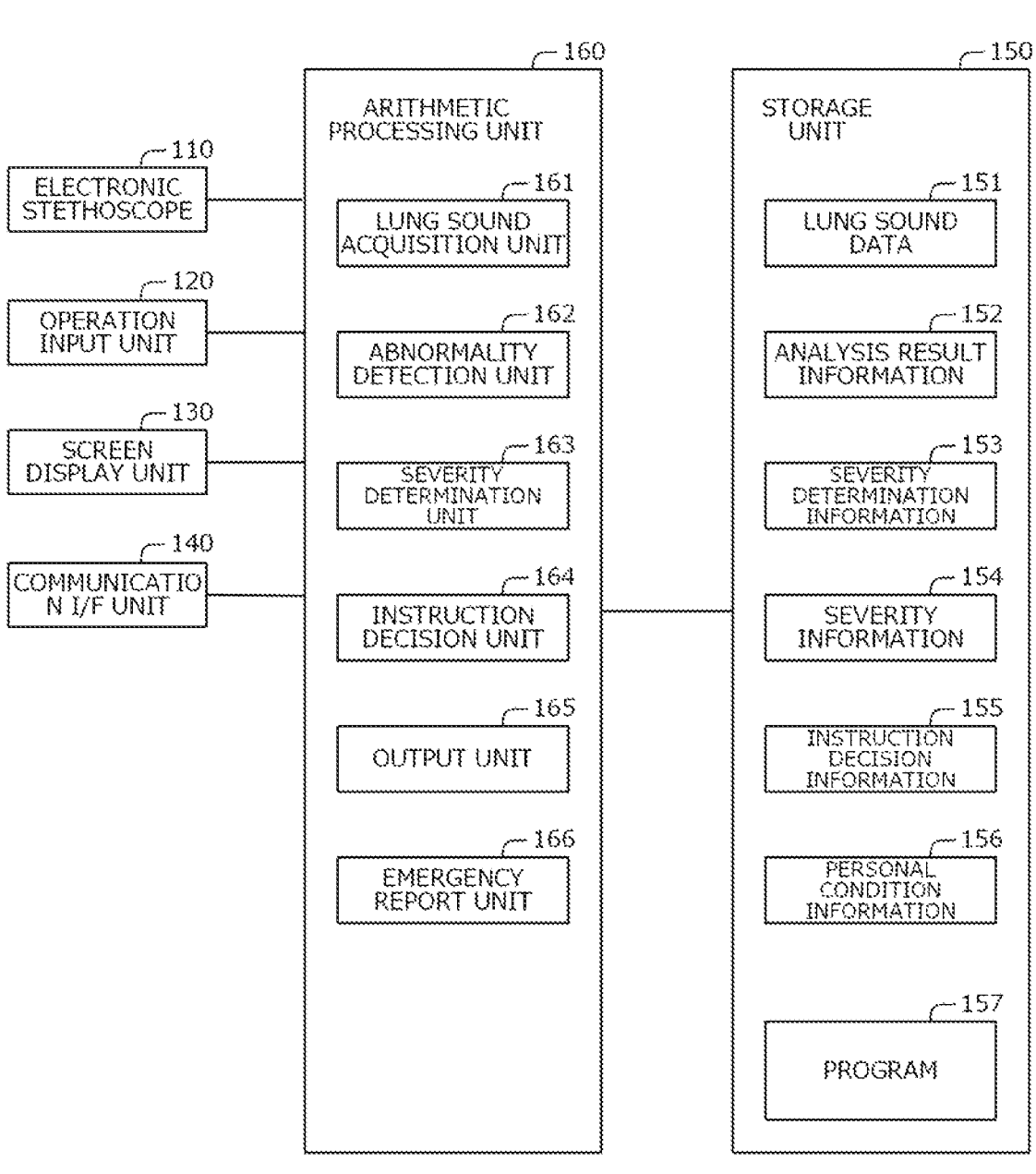
FIG. 11 is a block diagram illustrating another exemplary configuration of an analysis device.

A first exemplary embodiment of the present invention will be described with reference to FIGS. 1 to 11. FIG. 1 is a block diagram illustrating an exemplary configuration of an analysis device 100. FIG. 2 illustrates an example of lung sound data 151. FIGS. 3 and 4 are diagrams for explaining exemplary auscultation positions. FIG. 5 illustrates an example of analysis result information 152. FIG. 6 illustrates an example of severity determination information 153. FIG. 7 illustrates an example of severity information 154. FIG. 8 illustrates an example of instruction decision information 155. FIG. 9 illustrates exemplary information included in personal condition information 156. FIG. 10 is a flowchart illustrating an exemplary operation of the analysis device 100. FIG. 11 is a block diagram illustrating another exemplary configuration of an analysis device.

In the first exemplary embodiment, the analysis device 100 that outputs an instruction corresponding to a result of analyzing lung sounds will be described. As described below, the analysis device 100 acquires lung sounds from a plurality of positions on the posterior side and the anterior side of the chest, and detects abnormality in each position based on the acquired lung sounds. The analysis device 100 also determines the severity of heart failure based on the detected result. Then, the analysis device 100 decides an instruction to a user based on the determined severity. Then, the analysis device 100 outputs the decided instruction to the user and the like.

The analysis device 100 also includes personal condition information 156 representing the condition of a person. When determining the severity of heart failure and deciding an instruction according to the severity, the analysis device 100 can utilize the personal condition information 156.

The analysis device 100 is an information processing device that analyzes lung sounds acquired from a patient and outputs an instruction according to the analysis result. The analysis device 100 may be a smartphone, a tablet terminal, a personal digital assistant (PDA), a laptop personal computer, or the like, for example. The analysis device 100 may be one other than that mentioned above as an example.

FIG. 1 illustrates an exemplary configuration of the analysis device 100. Referring to FIG. 1, the analysis device 100 includes, for example, an electronic stethoscope 110, an operation input unit 120, a screen display unit 130, a communication I/F unit 140, a storage unit 150, and an arithmetic processing unit 160, as main constituent elements.

The electronic stethoscope 110 acquires lung sounds of a patient. For example, when the chest piece of the stethoscope is attached to the posterior side or the anterior side of the chest of a patient, the electronic stethoscope 110 converts the lung sounds of the patient into digital signals, and transfer them to the arithmetic processing unit 160 in a wireless or wired manner.

The operation input unit 120 is configured of operation input devices such as a keyboard and a mouse. The operation input unit 120 detects operation by a user who uses the analysis device 100, and outputs it to the arithmetic processing unit 160. The users may include a medical professional such as a nurse, caring staff such as a care worker, and family of the patient, besides the patient.

The screen display unit 130 is a screen display device such as a liquid crystal display (LCD). The screen display unit 130 displays, on the screen, various types of information such as an analysis result, in response to an instruction from the arithmetic processing unit 160.

The communication I/F unit 140 is configured of a data communication circuit. The communication I/F unit 140 performs data communication with various external devices such as a server device connected via a wired or wireless manner.

The storage unit 150 is a storage device such as a hard disk or a memory. The storage unit 150 stores therein processing information and a program 157 required for various types of processing performed in the arithmetic processing unit 160. The program 157 is read and executed by the arithmetic processing unit 160 to thereby implement various processing units. The program 157 is read in advance from an external device or a storage medium via the data input/output function of the communication I/F unit 140 and the like, and is stored in the storage unit 150. Main information stored in the storage unit 150 includes, for example, lung sound data 151, analysis result information 152, severity determination information 153, severity information 154, instruction decision information 155, and personal condition information 156.

The lung sound data 151 represents lung sound data of each auscultation position. FIG. 2 illustrates an example of information included in the lung sound data 151. Referring to FIG. 2, the lung sound data 151 includes lung sound data of each auscultation position, for example.

The information as illustrated in FIG. 2 included in the lung sound data 151 is created each time analysis is performed using the analysis device 100 or each time auscultation is performed using the electronic stethoscope 110, for example. The lung sound data 151 may be a combination of data identification information corresponding to the auscultation date/time or the like and the information as illustrated in FIG. 2.

Here, the field of auscultation position in the information included in the lung sound data 151 indicates an approximate position of the body of a patient to which the chest piece of the electronic stethoscope 110 is applied for auscultation of the lung sounds. That is, the auscultation position is a position for acquiring the lung sounds. For example, in the example of FIG. 2, twelve positions in total from an auscultation position (1) to an auscultation position (12) are set (in FIG. 2, auscultation positions (3) to (11) are omitted).

FIG. 3 is a schematic diagram for explaining examples of the auscultation positions (1) to (6), and FIG. 4 is a schematic diagram for explaining examples of the auscultation positions (7) to (12). Referring to FIG. 3, the auscultation positions (1) and (2) are set at left and right of the upper lung field on the posterior side of the chest, for example. The auscultation positions (3) and (4) are set at left and right of the middle lung field on the posterior side of the chest, for example. The auscultation positions (5) and (6) are set at left and right of the lower lung field on the posterior side of the chest, for example. Referring to FIG. 4, the auscultation positions (7) and (8) are set at left and right of the upper lung field on the anterior side of the chest. The auscultation positions (9) and (10) are set at left and right of the middle lung field on the anterior side of the chest. The auscultation positions (11) and (12) are set at left and right of the lower lung field on the anterior side of the chest. As described above, the auscultation positions are set in advance, for example.

Note that the auscultation positions are not limited to the number and the positions described above. For example, not only the posterior side and the anterior side of the chest, it is also possible to set auscultation positions in the upper lung field, the middle lung field, and the lower lung field of the left and right side chest parts to have eighteen positions in total. Alternatively, some of the above-described auscultation positions may be excluded. For example, it is possible to exclude the auscultation positions (3) to (6), (9), and (10) to thereby limit the positions to six positions in total, that is, the auscultation positions (1), (2), (7), (8), (11), and (12).

Further, in the field of lung sound data of the lung sound data 151, digital time-series acoustic signals including lung sounds obtained by the electronic stethoscope 110 at an auscultation position are recorded. The posture of the patient at the time of auscultation is roughly classified into a lying position and a sitting position. The auscultation of the posterior side of the chest and the anterior side of the chest is generally performed in a sitting position. The signal length of one piece of lung sound data (for example, data 1) may have any length. One piece of lung sound data may include signals of continuous N times of respiration of a patient. Here, N represents a positive integer of 1 or larger. The lung sound data may be signals in which processing such as removal of time-series acoustic signals during a period of a pause phase, noise removal, and application of respiration timing is performed on the time-series acoustic signals obtained from the electronic stethoscope 110.

The analysis result information 152 indicates a result of detecting abnormality based on the lung sound data 151 by an abnormality detection unit 162 to be described below. FIG. 5 illustrates an example of information included in the analysis result information 152. Referring to FIG. 5, the analysis result information 152 includes an analysis result of each auscultation position, for example.

The information as illustrated in FIG. 5 included in the analysis result information 152 is created each time analysis is performed using the analysis device 100 or analysis is performed on the lung sound data 151 by the abnormality detection unit 162, for example. The analysis result information 152 may be a combination of analysis result identification information corresponding to the date/time on which the abnormality detection unit 162 performed analysis or the like and the information as illustrated in FIG. 5.

In the analysis result field of the information included in the analysis result information 152, a result of mechanically analyzing the lung sound data by the abnormality detection unit 162, described below, is recorded. For example, in the analysis result field, a numerical value indicating whether or not the lung sound data is abnormal lung sound data is recorded. For example, the analysis result field may contain a binary value, that is, a value 0 indicating normal lung sounds or a value 1 indicating abnormal lung sounds. Alternatively, the analysis result field may contain a numerical value representing the abnormal degree of the lung sound data. Regarding the abnormal degree, an abnormal degree that is equal to or less than a preset threshold represents that the lung sound data is normal lung sounds, and an abnormal degree exceeding the threshold represents that the lung sound data is abnormal lung sounds.

The severity determination information 153 is information used to determine the severity by the severity determination unit 163 to be described below. The severity determination information 153 is, for example, acquired in advance by a method such as being read from an external device or a storage medium via the data input/output function of the communication I/F unit 140 or the like, being input through operation of the operation input unit 120 by the user, or the like, and is stored in the storage unit 150. The severity determination information 153 may be created at the timing when the patient is discharged from hospital. In other words, the severity determination information 153 may be created according to the condition of the patient at the time of discharge from hospital. In general, most of hospitalized heart failure patients leave hospital in a remission state after receiving a heart failure treatment. Therefore, the lung sounds at the time of discharge from hospital are normal in most patients. However, there is a case where a patient is discharged from hospital in a mild case due to the circumstances of the patient. By creating the severity determination information 153 according to the condition at the time of discharge from hospital, it is possible to perform determination according to the condition of the patient at the time of discharge from the hospital such as a patient who left the hospital in a remission state or a patient who left the hospital in a mild case. The severity determination information 153 may be created or updated at the timing when a patient attends hospital.

FIG. 6 illustrates an example of the severity determination information 153. Referring to FIG. 6, the severity determination information 153 is a table that includes, for example, a column corresponding to each of the auscultation positions (1) to (12) one to one, and a row corresponding to a degree of severity one to one. At an intersection between a column and a row, a + sign indicating that there is abnormality in the lung sounds or a − sign indicating that there is no abnormality in the lung sounds are set. For, example, in the example illustrated in FIG. 6, the table of the severity determination information 153 indicates that the severity is determined to be severity 0 when there is no abnormality in lung sounds at any auscultation positions. When there is abnormality in the lung sounds at at least one of the auscultation positions (11) and (12) set in the lower lung field in the anterior side of the chest and there is no abnormality in the lung sounds at the other auscultation positions (1) to (10), it is determined that the severity is 1. Further, when there is abnormality in the lung sounds at both the auscultation positions (11) and (12), there is abnormality in the lung sounds at either one of the auscultation positions (5) and (6) set in the lower lung field of the posterior side of the chest, and there is no abnormality in the lung sounds in the other auscultation positions (1) to (4) and (7) to (10), it is determined that the severity is 2. The severity N set in the last row means that there is abnormality in the lung sounds at all auscultation positions (1) to (12). In FIG. 6, although description of one or more degrees of severity are omitted between the severity 2 and the severity N, auscultation positions having abnormality in the lung sounds and auscultation positions not having abnormality in the lung sounds are also set for them. In the one or more degrees of severity between the severity 2 and the severity N, the number of auscultation positions at which there is abnormality in the lung sounds is four or larger and less than twelve, and the number increases as closer to the severity N.

As described above, in the severity determination information 153, the severity of heart failure is classified into N+1 classes from the severity 0 to the severity N, depending on the combination of presence or absence of abnormality in the lung sounds at the auscultation positions (1) to (12), for example. Here, the severity 0 is a state where no abnormal lung sound is heard. Therefore, it can be said that heart failure is remitted. The severity 1 is a condition in which abnormal lung sounds are heard only in the lower lung field of the anterior side of the chest. Therefore, heart failure is mild although not remitted, and is a condition in which some patients are discharged from hospital in such a condition. The severity 2 is a condition in which abnormal lung sounds are heard in one of the lower lung field of the posterior side of the chest in addition to the lower lung field of the anterior side of the chest. Therefore, it can be said that it is more severe than the severity 1. However, it still belongs to the mild case, so there is a high possibility of preventing re-hospitalization if it is treated appropriately at this point.

Note that the information shown in the severity determination information 153 is not limited to that illustrated in FIG. 6. The severity determination information 153 may indicate information other than that illustrated in FIG. 6. For example, the case where there is abnormality in lung sounds at at least one of the auscultation positions (11) and (12) set in the lower lung field of the anterior side of the chest and there is no abnormality in lung sounds at the other auscultation positions (1) to (10), and the case where there is abnormality in lung sounds at both of the auscultation positions (11) and (12), there is abnormality in lung sounds at at least one of the auscultation positions (5) and (6), and there is no abnormality in lung sounds at the other auscultation positions (1) to (4) and (7) to (10), may be set to be severity 1. The number of columns of the severity determination information 153 may correspond to the number of the auscultation positions previously set in the lung sound data 151.

Further, it is known that when rales are heard at the end of inspiration, it is mild, and when the rales are heard immediately after the start of inspiration, it is severe. Therefore, in addition to presence or absence of abnormal lung sounds at each auscultation position, the timing that the abnormal lung sounds are heard may be added to the determination table, and the severity of the heart failure may be determined according to the combination of an auscultation position, presence or absence of abnormal lung sounds, and the timing that the abnormal lung sounds are heard. In the severity determination information 153, the degrees of severity may be set corresponding to the type and the number of abnormal sounds such as rales having different characteristics (rough discontinuous rales, fine continuous rales). Further, in the severity determination information 153, the degrees of severity may be set corresponding to information that may be included in the personal condition information 156 such as the amount of weight increase of the patient. Further, the severity determination information 153 may be information in which the number of auscultation positions at which abnormal lung sounds are heard and the severity of heart failure of the patient are associated with each other, for example. For example, in the severity determination information 153, the severity may be set to be 0, 1, 2, 3, or 4 (maximum) when the number of auscultation positions at which abnormal lung sounds are heard is 0, 1 to 2, 3 to 4, 5 to 8, or 9 or more, respectively.

The severity information 154 shows a result determined by the severity determination unit 163 to be described below by using the analysis result information 152 and the severity determination information 153. FIG. 7 illustrates an example of the analysis result information 152. Referring to FIG. 7, in the severity information 154, severity identification information corresponding to the date/time when the severity determination unit 163 performed determination and the severity are associated with each other, for example.

In the field of severity in the severity information 154, a result determined by the severity determination unit 163 using the analysis result information 152 and the severity determination information 153 is recorded. That is, information indicating the above-described severity such as severity 0, severity 1, severity 2, and the like is recorded.

The instruction decision information 155 is information to be used for deciding an instruction corresponding to the severity by the instruction decision unit 164 to be described below. The instruction decision information 155 is, for example, acquired in advance by a method such as being read from an external device or a storage medium via the data input/output function of the communication I/F unit 140 or the like, being input through operation of the operation input unit 120 by the user, or the like, and is stored in the storage unit 150. Similar to the severity determination information 153, the instruction decision information 155 may be created at the timing when a patient is discharged from hospital. By creating the instruction decision information 155 according to the condition at the time of discharge from hospital, it is possible to perform decision corresponding to the condition of the patient at the time of discharge from hospital such as a patient who left the hospital in a remission state or a patient who left the hospital in a mild case. The instruction decision information 155 may be created or updated at the timing when the patient attends hospital.

FIG. 8 illustrates an example of the instruction decision information 155. Referring to FIG. 8, the instruction decision information 155 shows the content of instruction for each severity, for example. For example, the first row of FIG. 8 shows a next examination instruction that indicates instructing date and time of the next examination when the severity is 0, 1, or 2.

In the example of FIG. 8, the severity 0 to 2 and the instruction content "next examination instruction" are associated with each other. The severity 3 to 4 and the instruction content "medication instruction" are associated with each other. The severity 5 to N and the instruction content "seeking diagnosis instruction" are associated with each other. Here, in the case of "next examination instruction", for example, date and time of examination and analysis using the analysis device 100, such as next examination three hours later or next examination one day later, will be instructed. The period of time to the next examination is previously set for example. Further, in the case of "medication instruction", taking previously set medicine will be instructed. Further, in the case of "seeking diagnosis instruction", seeking diagnosis will be instructed. In the case of "seeking diagnosis instruction", date and time of seeking diagnosis, such as seeking diagnosis today or seeking diagnosis tomorrow, will be instructed.

Note that the instruction content may be one other than that illustrated above as an example. For example, the instruction content may be a combination of the contents illustrated above such as to instruct next examination after medication. Further, the instruction content may be further narrowed down such that the period of time to the next examination or date of the next examination may differ between the case where the severity is 0 and the case where the severity is 1. In the instruction decision information 155, an instruction corresponding to the information that may be included in the personal condition information 156 may be set such as narrowing down the instruction content according to the medication condition.

The personal condition information 156 is information representing the condition of the patient. The information included in the personal condition information 156 can be used for determining the severity by the severity determination unit 163 or deciding the instruction by the instruction decision unit 164. The personal condition information 156 is, for example, acquired in advance by a method such as being read from an external device or a storage medium via the data input/output function of the communication I/F unit 140 or the like, being input through operation of the operation input unit 120 by the user, or the like, and is stored in the storage unit 150. The personal condition information 156 may be appropriately updated by, for example, operating the operation input unit 120 each time analysis using the analysis device 100 is performed FIG. 9 illustrates exemplary information included in the personal condition information 156. Referring to FIG. 9, in the personal condition information 156, condition identification information corresponding to the date/time that the condition information was input and the condition information are associated with each other, for example.

In the condition information field in the personal condition information 156, information representing the weight and the medication of the patient may be included. The information representing the medication may include information such as date/time that the patient took medicine last time, the type of medicine taken by the patient last time, and medication frequency. Further, the condition information field may include information representing blood pressure, pulse, subjective symptoms (short breath when goes out, edema, cough, anorexia, or the like), water intake, percutaneous arterial blood oxygen saturation (SPO2), or the like. The condition information field may also include informative matters from a doctor at the time of discharge from hospital or at the time of attending hospital.

The main information stored in the storage unit 150 is as described above. Note that various types of identification information such as data identification information, analysis result identification information, severity identification information, and condition identification information may be different respectively, or may be common information such as information corresponding to date/time of the entire analysis, for example.

The arithmetic processing unit 160 has a microprocessor such as a CPU and the peripheral circuits thereof, and is configured to read and execute the program 157 from the storage unit 150 to allow the hardware and the program 157 to cooperate with each other to thereby implement the various processing units. The main processing units implemented by the arithmetic processing unit 160 include the lung sound acquisition unit 161, the abnormality detection unit 162, the severity determination unit 163, the instruction decision unit 164, and the output unit 165.

The lung sound acquisition unit 161 acquires digital time-series acoustic signals including lung sounds of a patient and other information. The lung sound acquisition unit 161 acquires digital time-series acoustic signals including lung sounds of a patient from the electronic stethoscope 110, in accordance with an instruction by a user input from the operation input unit 120 or the like. The lung sound acquisition unit 161 can also acquire information indicating date/time and the like, along with the digital time-series acoustic signals. Then, the lung sound acquisition unit 161 generates the lung sound data 151 as illustrated in FIG. 2 by using the acquired digital time-series acoustic signals and the other information, and stores it in the storage unit 150. As described above, the lung sound acquisition unit 161 may combine the data identification information and the information as illustrated in FIG. 2.

Note that any method may be used to acquire lung sounds of each auscultation position of a patient by an electronic stethoscope and record it in association with the auscultation position. For example, as described in Patent Literature 1, 4, 6 or the like, a method in which a guidance screen for guidance on the auscultation position to an operator who uses the electronic stethoscope 110 is shown on the screen display unit 130, or the like may be used. The lung sound acquisition unit 161 may instruct the breath timing to a patient by the method as described in Patent Literature 8.

The lung sound acquisition unit 161 may be configured to calculate an index value for the quality of lung sounds and give warning based on the calculated index value on the screen display unit 130. With such warning, a patient, a user, or the like can acquire lung sounds again after taking measures to reduce the background noise and/or increase the lung sounds.

An index value calculation process for the quality of lung sounds is performed by calculating and comparing the signal intensities after applying a predetermined filter, for example. For example, the lung sound acquisition unit 161 uses a bandpass filter to extract time-series acoustic signals in the frequency band of 100 Hz to about 2 kHz in which lung sounds of a patient are included, from the time-series acoustic signals output from the electronic stethoscope 110. Then, the lung sound acquisition unit 161 calculates the intensity of the lung sounds and the intensity of the background noise in the extracted time-series acoustic signals, and calculates the difference degree thereof as an index value of the quality of the lung sounds. For example, the lung sound acquisition unit 161 detects an inspiratory phase, an expiratory phase, and a pause phase from the time-series acoustic signals including lung sounds. Then, the lung sound acquisition unit 161 calculates the intensity of the time-series acoustic signals in the pause phase as the intensity of the background noise. As the intensity of the time-series acoustic signals, a root-mean-square of the amplitude value may be used for example. However, it is not limited thereto, and may be an amplitude or the like. Further, the lung sound acquisition unit 161 calculates a value obtained by subtracting the intensity of the background noise from the intensity of the time-series acoustic signals in the inspiratory phase and/or expiratory phase, as the intensity of the lung sounds. Then, the lung sound acquisition unit 161 uses the ratio of the calculated intensity of the lung sounds to the intensity of the background noise, as an index value of the quality of the lung sounds. Note that an index value of the quality of the lung sounds is not limited to that described above. It is also possible to use an S/N ratio calculated from the intensity of the lung sounds and the intensity of the background noise as an index value. Application of a filter may be omitted.

Note that the lung sound acquisition unit 161 can detect an expiratory phase and an inspiratory phase by comparing the time-series acoustic signals with a predetermined threshold. The lung sound acquisition unit 161 can also detect a predetermined period immediately before the detected inspiration start point of time as a pause phase. The lung sound acquisition unit 161 may detect the inspiratory phase, the expiratory phase, and the pause phase by using a method other than that illustrated above. For example, the lung sound acquisition unit 161 may be configured to acquire estimated probability of an inspiratory phase, an expiratory phase, and a pause phase for each section from a learning model, by inputting time-series acoustic signals including the lung sounds of the patient into a learning model having been learned through machine learning for estimating which section of the time-series acoustic signals including the lung sounds output from the electronic stethoscope 110 is an inspiratory phase, an expiratory phase, or a pause phase. A learning model can be generated in advance through machine learning using a machine learning algorism such as a neural network by using time-series acoustic signals including various lung sounds as teacher data.

Further, the lung sound acquisition unit 161 may remove the period of a pause phase and the background noise from the digital time-series acoustic signals including the lung sounds, and records, in the lung sound data 151, the digital time-series acoustic signals after removal of the period of the pause phase and the background noise, in association with the auscultation position. For example, the lung sound acquisition unit 161 divides the digital time-series acoustic signals including the lung sounds into two, that is, a section configured of an inspiratory phase and an expiratory phase immediately thereafter (hereinafter referred to as an inspiratory/expiratory section), and a section of a pause phase (hereinafter referred to as a pause section). Then, the lung sound acquisition unit 161 calculates the frequency spectrum of the inspiratory/expiratory section and the pause section by applying fast Fourier transform (FFT) to the digital time-series acoustic signals in each of the inspiratory/expiratory section and the pause section. Then, the lung sound acquisition unit 161 subtracts the frequency spectrum of the pause section from the frequency spectrum of the inspiratory/expiratory section. By the subtraction, the background noise included in the inspiratory phase and the expiratory phase is suppressed. Then, the lung sound acquisition unit 161 applies inverse frequency transform to the frequency spectrum of the inspiratory/expiratory section to thereby generate digital time-series acoustic signals after the removal of the noise in the inspiratory/expiratory section. Then, the lung sound acquisition unit 161 records the generated digital time-series acoustic signals after the removal of the noise in the inspiratory/expiratory section, in the lung sound data 151 in association with the auscultation position. Note that the lung sound acquisition unit 161 may remove the period of a pause phase from the digital time-series acoustic signals including the lung sounds of the auscultation position and not remove the background noise. In that case, the lung sound acquisition unit 161 divides the focused digital time-series acoustic signals including the lung sounds of the auscultation position into two, that is, the inspiratory/expiratory section and the pause section, and records the digital time-series acoustic signals in the inspiratory/expiratory section in the lung sound data 151, in association with the auscultation position.

The abnormality detection unit 162 detects abnormality from lung sound data of each auscultation position included in the lung sound data 151, and records the detection result in the analysis result information 152 in association with the auscultation position. For example, the abnormality detection unit 162 inputs the lung sound data into an abnormality detection model previously generated and stored, and acquires the probability that the lung sound data is abnormal lung sounds from the abnormality detection model. Then, the abnormality detection unit 162 compares the probability of abnormal lung sounds with a preset threshold. Then, when the probability exceeds the threshold, the abnormality detection unit 162 determines that the data is abnormal lung sounds. This means that the abnormality detection unit 162 detects abnormality. On the other hand, when the probability is equal to or smaller than the threshold, the abnormality detection unit 162 determines that the data is not abnormal lung sounds. Then, the abnormality detection unit 162 records the detection result in the analysis result information 152.

Note that the abnormality detection model can be generated in advance by, for example, generating teacher data by using a database in which abnormal sounds are collected, and learning characteristics of input sound data (input data) and determination criteria by using deep learning. For example, the abnormality detection unit 162 can use, for leaning and input data, a spectrum program in which sounds are applied with fast Fourier transform (FFT) or log-FFT for each certain section to be aligned in the time-series manner, and for deep learning, recurrent neural network (RNN) or convolutive neural network (CNN) can be used.

Further, the abnormality detection unit 162 may use a method in which a lung sound waveform is transformed into a short-time feature amount such as zero-cross coefficient or mel-frequency cepstral coefficient (MFCC) and abnormal sounds are detected by machine learning. For example, the abnormality detection unit 162 may perform modeling by mixed Gaussian distribution (GMM) at the time of learning, and check whether or not it matches the model at the time of detection. Further, the abnormality detection unit 162 may learn the identifying surface of an identifier such as a support vector machine (SVM) and uses the identifying surface to identify whether or not the input data corresponds to the abnormal sounds. The abnormality detection unit 162 may generate the feature amount by using the data itself like non-negative matrix factorization (NMF) or principal component analysis (PCA), other than the method of directly calculating the feature amount as described above.

Further, the abnormality detection unit 162 may detect abnormal sounds by the decision tree using statistical features of an input waveform such as long-time power distribution of input signals, distribution of component amount/component ratio of a specific frequency bin range, or the like. In that case, as items of the decision tree, the abnormality detection unit 162 may use statistical features (for example, when a process frame larger than $3\sigma$ is generated by Gaussian approximation), rather than a direct value (for example, when the power exceeds 20 mW for three consecutive frames). Further, the abnormality detection unit 162 may detect abnormal sounds by not using the input signal itself but modeling it through auto-regression (AR) process or the like and detecting abnormal sounds when some of the model parameters exceed a threshold. These methods may not include a learning process, but includes observation of abnormal sounds that are object signals in the configuration of the decision tree or determination of a threshold. Therefore, they are included in supervised learning for the sake of convenience.

Further, the abnormality detection unit 162 may be configured to learn an abnormality detection model by using past lung sound data of the patient and auscultation observations at the time of discharge from hospital or the like, for example. As lung sound data to be used for learning an abnormality detection model, in addition to the lung sound data of the patient at the time of discharge from hospital, it is also possible to use normal lung sound data of the patient before it or use normal lung sound data of a person other than the patient. By generating an abnormality detection model on the basis of lung sound data at the time of discharge from hospital, it is possible to perform detection in consideration of the condition of the patient at the time of discharge from hospital.

Note that an abnormality detection model may be generated for each auscultation position, or may be shared by a plurality of auscultation positions. Further, abnormality detection models may be a plurality of models that are machine-learned from different viewpoints. For example, abnormality detection models may include a model in which lung sounds of the same auscultation position is divided into a lung sound portion of the inspiratory phase, a lung sound portion of the expiratory phase, and a portion other than those (that is, pause phase) on the basis of the breath timing, and learning is performed by using the lung sound portion of the inspiratory phase, and a model obtained through learning by using the lung sound portion of the expiratory phase.

The severity determination unit 163 determines the severity, on the basis of the analysis result of each auscultation position indicated by the analysis result information 152, and the severity determination information 153. Then, the severity determination unit 163 stores the determined severity in association with the severity identification information in the storage unit 150 as the severity information 154.

For example, the severity determination unit 163 refers to the analysis result information 152 to specify the auscultation position in which abnormality is detected. Then, the severity determination unit 163 refers to the severity determination information 153 to determine the severity corresponding to the specified result.

As described above, the severity determination information 153 can be created according to the condition of the patient at the time of discharge from hospital. In the case where the severity determination information 153 is created as described above, the severity determination unit 163 may also refer to the severity determination information 153 corresponding to the condition of the patient at the time of discharge from hospital to determine the severity corresponding to the condition of the patient at the time of discharge from hospital.

Moreover, the severity determination unit 163 may be configured to revise the determined severity by referring to the personal condition information 156 when determining the severity. For example, there is an observation that weight increases due to accumulation of water in lungs when the heart failure gets worse. Therefore, the severity determination unit 163 can revise the determined severity on the basis of the weight of the patient included in the personal condition information 156. For example, when a predetermined condition is satisfied such as the weight increasing by 3 kg in a week, the severity determination unit 163 can revise the severity by a set value such as incrementing the determined severity by 1. Note that the severity determination unit 163 may perform revision other than that described above such as incrementing the severity by 2 when the weight increases by 5 kg in a week. Further, the severity determination unit 163 may perform revision using the personal condition information 156 other than that described above, by, for example, incrementing the severity when the blood pressure is lowered by a predetermined value or more or the pulse exceeds a predetermined number. The severity determination unit 163 may directly determine the severity in consideration of the personal condition information 156 by referring to the severity determination information 153 in which severity is set according to the information that may be included in the personal condition information 156.

The instruction decision unit 164 decides an instruction on the basis of the severity indicated by the severity information 154 and the instruction decision information 155. For example, the instruction decision unit 164 decides an instruction by specifying the instruction content corresponding to the severity indicated by the severity information 154 in the instruction decision information 155.

As described above, the instruction decision information 155 can be created according to the condition of the patient at the time of discharge from hospital. In the case where the instruction decision information 155 is created as described above, the instruction decision unit 164 may also refer to the instruction decision information 155 corresponding to the condition of the patient at the time of discharge from hospital to decide the instruction corresponding to the condition of the patient at the time of discharge from hospital.

Moreover, the instruction decision unit 164 may be configured to revise the decided instruction by referring to the personal condition information 156 when deciding the instruction. For example, it is assumed that a predetermined condition such as taking medicine at determined intervals is satisfied, on the basis of information indicating medication included in the personal condition information 156. In that case, the severity gets worse although the condition is satisfied, so it is assumed that effectiveness of the medicine is lowered, for example. Accordingly, the instruction decision unit 164 can revise the instruction according to the predetermined revision policy such as revising to an instruction for the case where the severity is incremented by 1, instructing seeking diagnosis regardless of the severity, or the like. The instruction decision unit 164 may directly determine the instruction in consideration of the personal condition information 156 by referring to the instruction decision information 155 in which instruction is set corresponding to the information that may be included in the personal condition information 156.

The output unit 165 displays the instruction decided by the instruction decision unit 164 on the screen display unit 130. The output unit 165 can be configured to transmit the instruction decided by the instruction decision unit 164, the lung sound data 151, the analysis result information 152, the severity information 154, previously input information, and the like to an external device having been set. For example, the instruction decision unit 164 may be configured to transmit the lung sound data 151, the analysis result information 152, the severity information 154, previously set therapy policy information, and the like to an external device having been set, when the severity exceeds a transmission threshold. Note that an external device that is a transmission destination of the output unit 165 may be a mobile information terminal held by a patient, a mobile information terminal or an information processing device held by a doctor such as a home doctor or a medical institution, or the like. Further, the input therapy policy information may include information indicating presence or absence, the type, or the like of the therapy that the patient does not wish to take. Further, output to an external device by the output unit 165 may be realized by using at least one of arbitrary communication methods such as email, a messaging function of groupware, business chat, and the like.

Next, an exemplary operation of the analysis device 10 will be described with reference to FIG. 10.

Referring to FIG. 10, the lung sound acquisition unit 161 acquires digital time-series acoustic signals including lung sounds of a patient or the like, for each auscultation position (step S101). Then, the lung sound acquisition unit 161 generates the lung sound data 151 as illustrated in FIG. 2 by using the acquired digital time-series acoustic signals and the other information, and stores it in the storage unit 150. As described above, the lung sound acquisition unit 161 may combine data identification information and the information as illustrated in FIG. 2.

When acquiring the digital time-series acoustic signals, the lung sound acquisition unit 161 may calculate an index value for the quality of lung sounds and give warning based on the calculated index value on the screen display unit 130. The lung sound acquisition unit 161 may generate lung sound data 151 by using data after performing processing such as removal of time-series acoustic signals during a period of a pause phase, noise removal, and application of respiration timing, and store it in the storage unit 150.

The abnormality detection unit 162 detects abnormality from lung sound data of each auscultation position included in the lung sound data 151, and records the detection result in the analysis result information 152 in association with the auscultation position (step S102). For example, the abnormality detection unit 162 inputs the lung sound data into the abnormality detection model previously generated and stored, and acquires the probability that the lung sound data is abnormal lung sounds from the abnormality detection model. Then, the abnormality detection unit 162 compares the probability of abnormal lung sounds with a preset threshold. Then, when the probability exceeds the threshold, the abnormality detection unit 162 determines that the data is abnormal lung sounds. This means that the abnormality detection unit 162 detects abnormality. On the other hand, when the probability is equal to or smaller than the threshold, the abnormality detection unit 162 determines that the data is not abnormal lung sounds. Then, the abnormality detection unit 162 records the detection result in the analysis result information 152.

The severity determination unit 163 determines the severity on the basis of the analysis result of each auscultation position indicated by the analysis result information 152, and the severity determination information 153 (step S103). Then, the severity determination unit 163 stores the determined severity in association with the severity identification information, in the storage unit 150 as the severity information 154.

Note that the severity determination unit 163 may determine the severity corresponding to the condition of the patient at the time of discharge from hospital, by referring to the severity determination information 153 corresponding to the condition of the patient at the time of discharge from hospital. Moreover, the severity determination unit 163 may revise the determined severity by referring to the personal condition information 156 when determining the severity. The severity determination unit 163 may directly determine the severity in consideration of the personal condition information 156 by referring to the severity determination information 153 in which severity is set corresponding to the information that may be included in the personal condition information 156.

The instruction decision unit 164 decides an instruction on the basis of the severity indicated by the severity information 154 and the instruction decision information 155 (step S104). For example, the instruction decision unit 164 decides an instruction by specifying the instruction content corresponding to the severity in the instruction decision information 155.

Note that the instruction decision unit 164 may decide the instruction corresponding to the condition of the patient at the time of discharge from hospital, by referring to the instruction decision information 155 corresponding to the condition of the patient at the time of discharge from hospital. Moreover, the instruction decision unit 164 may revise the decided instruction by referring to the personal condition information 156 when deciding the instruction. The instruction decision unit 164 may directly determine the instruction in consideration of the personal condition information 156 by referring to the instruction decision information 155 in which instruction is set corresponding to the information that may be included in the personal condition information 156.

The output unit 165 displays the instruction decided by the instruction decision unit 164 on the screen display unit 130 (step S105). The output unit 165 can be configured to transmit the instruction decided by the instruction decision unit 164, the lung sound data 151, the analysis result information 152, the severity information 154, and the like to an external device having been set. For example, the instruction decision unit 164 may be configured to transmit the lung sound data 151, the analysis result information 152, the severity information 154, and the like to an external device having been set, when the severity exceeds a transmission threshold. Note that an external device that is a transmission destination of the output unit 165 may be a mobile information terminal held by a patient, a mobile information terminal or an information processing device held by a doctor such as a home doctor or a medical institution, or the like.

As described above, the analysis device 100 includes the abnormality detection unit 162, the severity determination unit 163, the instruction decision unit 164, and the output unit 165. According to such a configuration, the instruction decision unit 164 can decide the instruction by using the severity determined by the severity determination unit 163 on the basis of the detection result by the abnormality detection unit 162. As a result, the output unit 165 can output an instruction corresponding to the severity. Thereby, it is possible to output an appropriate instruction corresponding to the severity.

Further, the severity determination unit 163 and the instruction decision unit 164 can determine the severity and decide the instruction corresponding to the condition of the patient at the time of discharge from hospital. As a result, the severity determination unit 163 and the instruction decision unit 164 can make more appropriate determination and decision corresponding to the condition of the patient.

Further, the severity determination unit 163 and the instruction decision unit 164 can determine the severity and decide the instruction in consideration of the personal condition information 156. As a result, the severity determination unit 163 and the instruction decision unit 164 can perform more appropriate determination and decision corresponding to the condition of the patient.

Note that it is assumed that acquisition of lung sound data using the electronic stethoscope 110 may be terminated due to the circumstances of the patient or the like. In that case, the abnormality detection unit 162 performs analysis on the auscultation positions in which lung sound data has been acquired. The severity determination unit 163 may be configured to decide whether or nor to perform determination of severity, on the basis of the number of auscultation positions on which the abnormality detection unit 162 has performed analysis. For example, when the number of auscultation positions in which lung sound data has not been acquired and analysis of whether or not abnormal lung sounds has not been performed is smaller than a preset threshold, the severity determination unit 163 does not calculate severity and can display that the analysis is terminated in error on the screen display unit 130. This is because not to give erroneous information to the operator or the like. On the contrary, when the number of auscultation positions is equal to or larger than a preset threshold, the severity determination unit 163 assumes that no abnormal lung sound is detected at auscultation positions in which analysis of whether or not abnormal lung sounds are found has not been performed, and can calculate the severity. In that case, the severity determination unit 163 may hold the calculated severity as the most optimistic value. That is, when the calculated severity is the severity 1, it is not held as "severity 1" but can be held as "severity 1 or higher" or "at least severity 1". Note that the threshold may be set arbitrary.

Further, the analysis device 100 may be configured to determine on which auscultation position to be focused, on the basis of the auscultation position at which abnormality was detected in the past. For example, the lung sound acquisition unit 161 of the analysis device 100 can calculate the abnormality detection frequency for each auscultation position on the basis of the past analysis result information 152. Further, the lung sound acquisition unit 161 can give guidance to acquire lung sound data in the descending order of the calculated abnormality detection frequency. In the case of acquiring lung sound data in the descending order of the abnormality detection frequency, the threshold to be used for determining whether or not the severity determination unit 163 calculates the severity may be smaller, compared with the case of not acquired lung sound data in the descending order of the abnormal detection frequency.

Moreover, as illustrated in FIG. 11, the arithmetic processing unit 160 may include an emergency report unit 166, in addition to the respective processing units described above. The emergency report unit 166 makes an emergency report to an information processing terminal or the like of a doctor such as a home doctor or a medical institution when a predetermined reporting condition is satisfied.

A reporting condition may be set arbitrarily. For example, a reporting condition may be a condition corresponding to the situation after the output by the output unit 165. For example, a patient does not seek diagnosis within a set period after outputting an instruction for seeking diagnosis, re-examination is not taken within a set period although the next examination instruction was output, or the like. The reporting condition may be different for each severity, or the reporting condition may be set corresponding to the condition of the patient at the time of discharge from hospital. Moreover, the emergency report may include various types of information. For example, the emergency report can include at least one of a reporting condition serving as the cause of the emergency report, the lung sound data 151, the analysis result information 152, the severity information 154, the therapy policy information, and the like.

Second Exemplary Embodiment

Figure 12:
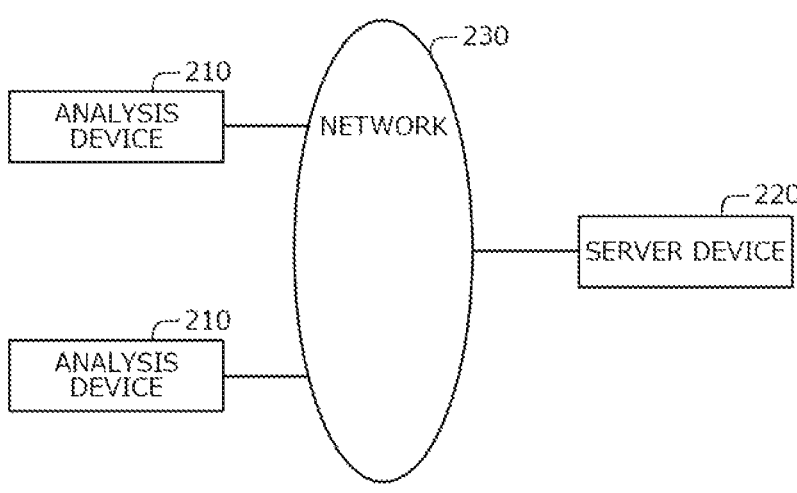
FIG. 12 illustrates an exemplary configuration of an analysis system according to a second exemplary embodiment of the present invention.

FIG. 12 is a block diagram of an analysis system 200 according to a second exemplary embodiment of the present invention. Referring to FIG. 12, the analysis system 200 is configured of a plurality of analysis devices 210 and a server device 220. The analysis devices 210 and the server device 220 are communicably connected with each other over a network 230 such as the Internet.

The analysis device 210 is an information processing device that outputs an instruction corresponding to a result of analyzing lung sounds. The analysis device 210 may be a smartphone, a tablet terminal, a PDA, a laptop personal computer, or the like, but is not limited thereto. The analysis device 210 includes an electronic stethoscope, a communication I/F unit, an operation input unit, a screen display unit, a storage unit, and an arithmetic processing unit that are not illustrated.

The server device 220 is a computer that provides, to the analysis devices 210, various services required for lung sound analysis over the network 230. For example, the server device 220 stores therein at least part of the lung sound data 151, the analysis result information 152, the severity determination information 153, the severity information 154, the instruction decision information 155, the personal condition information 156, and the program 157 illustrated in FIG. 1, and provides them to the analysis device 210 over the network 230. Therefore, the analysis device 210 is not needed to store at least part of the lung sound data 151, the analysis result information 152, the severity determination information 153, and the severity information 154, the instruction decision information 155, the personal condition information 156, and the program 157 in the storage unit 150 as compared with the analysis device 100 of FIG. 1, so that the memory capacity can be reduced.

Further, the server device 220 can also provide at least part of the functions of the lung sound acquisition unit 161, the abnormality detection unit 162, the severity determination unit 163, the instruction decision unit 164, and the output unit 165 illustrated in FIG. 1, to the analysis device 210 over the network 230. That is, the server device 220 executes at least a part of the processing illustrated in FIG. 10 in place of the analysis device 210. Therefore, in the analysis device 210, the configuration of the arithmetic processing unit 160 can be simplified as compared with the analysis device 100 of FIG. 1.

Third Exemplary Embodiment

Next, a third exemplary embodiment of the present invention will be described with reference to FIGS. 13 and 14. In the third exemplary embodiment, a configuration of an analysis device 300 will be described.

Figure 13:
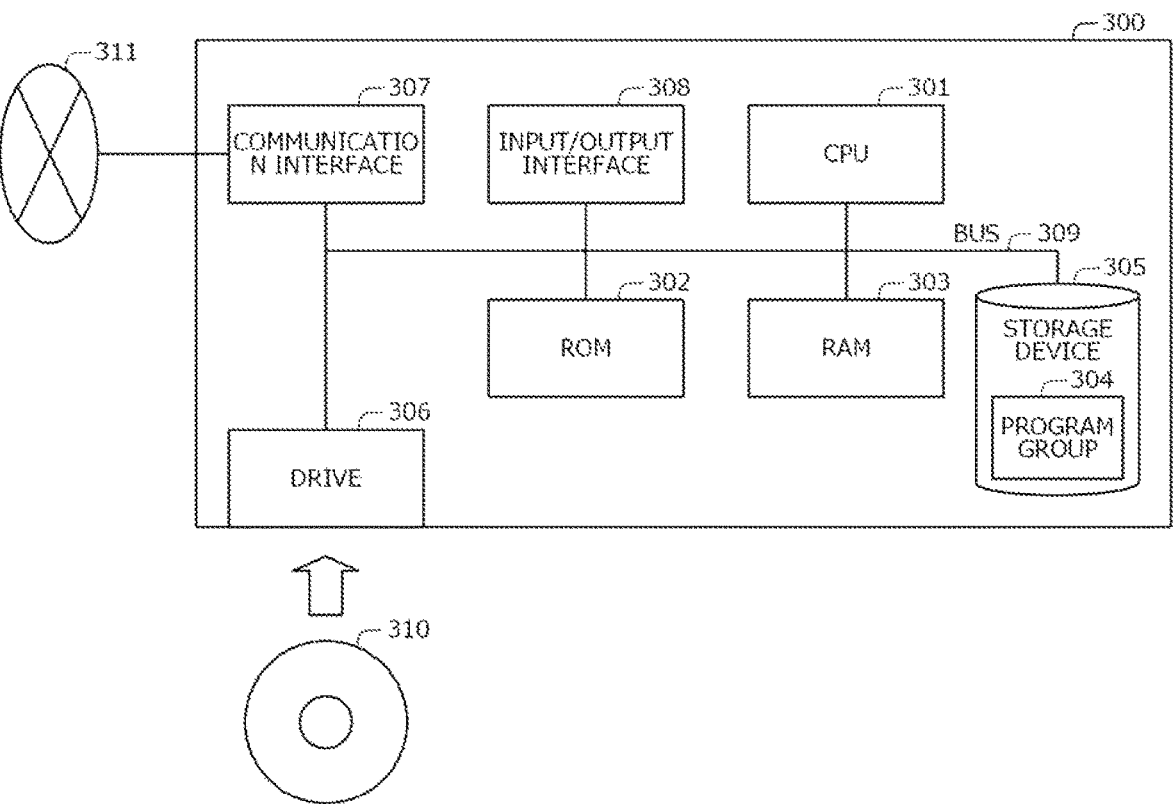
FIG. 13 illustrates an exemplary hardware configuration of an analysis device according to a third exemplary embodiment of the present invention.

FIG. 13 illustrates an exemplary hardware configuration of the analysis device 300. Referring to FIG. 13, the analysis device 300 includes a hardware configuration as described below, as an example.

Figure 14:
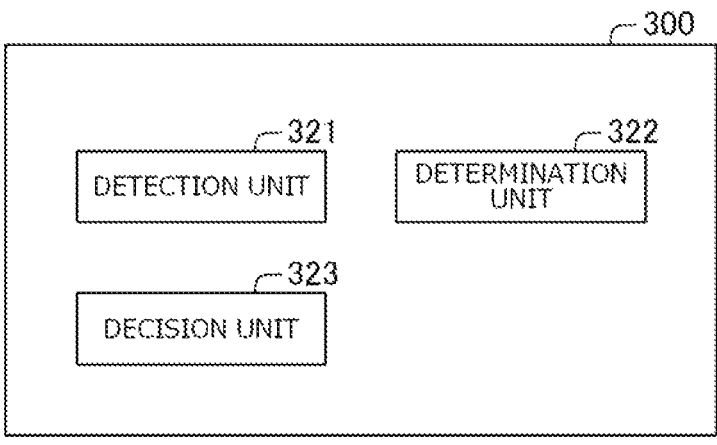
FIG. 14 is a block diagram illustrating an exemplary configuration of an analysis device.

Central Processing Unit (CPU) 301 (arithmetic device)
Read Only Memory (ROM) 302 (storage device)
Random Access Memory (RAM) 303 (storage device)
Program group 304 to be loaded to the RAM 303
Storage device 305 storing therein the program group 304
Drive 306 that performs reading and writing on a storage medium 310 outside the information processing device Communication interface 307 connecting to a communication network 311 outside the information processing device Input/output interface 308 for performing input/output of data Bus 309 connecting the respective constituent elements Further, the analysis device 300 can realize the functions as a detection unit 321, a determination unit 322, and a decision unit 323 illustrated in FIG. 14 through acquisition and execution of the program group 304 by the CPU 301. Note that the program group 304 is stored in the storage device 305 or the ROM 302 in advance, and is loaded to the RAM 303 by the CPU 301 as needed. Further, the program group 304 may be provided to the CPU 301 via the communication network 311, or may be stored on a storage medium 310 in advance and read out by the drive 306 and supplied to the CPU 301.

FIG. 13 illustrates an exemplary hardware configuration of the analysis device 300. The hardware configuration of the analysis device 300 is not limited to that described above. For example, the analysis device 300 may be configured of part of the configuration described above, such as without the drive 306.

The detection unit 321 detects abnormality in lung sounds for each auscultation position on the basis of time-series acoustic signals including lung sounds of each auscultation positions.

The determination unit 322 determines severity of the heart failure of a patient on the basis of a detection result of abnormality in the lung sounds of each auscultation position detected by the detection unit 321 and the condition information representing the condition of the patient.

The decision unit 323 decides an instruction to be output to the patient on the basis of the result of determination by the determination unit 322.

As described above, the analysis device 300 includes the detection unit 321, the determination unit 322, and the decision unit 323. According to such a configuration, the decision unit 323 can decide the instruction to be output to the patient by using the severity determined by the determination unit 322 on the basis of a detection result by the detection unit 321. As a result, it is possible to output an appropriate instruction corresponding to the severity. Further, since the determination unit 322 performs determination based on the condition information when determining the severity, the determination unit 322 can perform determination more accurately corresponding to the condition of the patient. As a result, it is possible to output a more appropriate instruction.

Note that the analysis device 300 as described above can be realized by incorporation of a predetermined program into an information processing device such as the analysis device 300. Specifically, a program that is another aspect of the present invention is a program for implementing, in an analysis device, a detection unit that detects abnormality in lung sounds for each auscultation position on the basis of time-series acoustic signals including lung sounds of each auscultation position, a determination unit that determines severity of heart failure of a patient on the basis of a detection result of abnormality in the lung sounds of each auscultation position detected by the detection unit and condition information representing the condition of the patient, and a decision unit that decides an instruction to be output to the patient on the basis of a result of determination by the determination unit.

Further, an analysis method to be implemented by an information processing device such as the analysis device 300 is a method including detecting abnormality in lung sounds for each auscultation position on the basis of time-series acoustic signals including lung sounds of each auscultation position, determining severity of heart failure of a patient on the basis of a detection result of abnormality in the lung sounds of each detected auscultation position and condition information representing the condition of the patient, and deciding an instruction to be output to the patient on the basis of a result of determination.

Since the invention of a program (or storage medium) or an analysis method having the above-described configuration also exhibits the same actions and effects as those of the analysis device 300, the above-described object of the present invention can be achieved.

While the present invention has been described with reference to the exemplary embodiments described above, the present invention is not limited to the above-described embodiments. The form and details of the present invention can be changed within the scope of the present invention in various manners that can be understood by those skilled in the art, such as a combination of various modifications.

INDUSTRIAL APPLICABILITY

The present invention is applicable to a device and a system for analyzing lung sounds of a person, and in particular, applicable to a device and a system for detecting, in an early stage, exacerbation of heart failure of a patient who received heart failure treatment and was discharged from hospital to prevent re-hospitalization.

The whole or part of the exemplary embodiments disclosed above can be described as, but not limited to, the following supplementary notes.

Supplementary Note 1

An analysis device comprising:

a detection unit that detects abnormality in lung sounds for each of auscultation positions on a basis of time-series acoustic signals including lung sounds of each of the auscultation positions;

a determination unit that determines severity of heart failure of a patient on a basis of a detection result of abnormality in the lung sounds of each of the auscultation positions detected by the detection unit and condition information representing a condition of the patient; and a decision unit that decides an instruction to be output to the patient on a basis of a result of the determination by the determination unit.

Supplementary Note 2

The analysis device according to supplementary note 1, wherein the determination unit determines the severity on a basis of the detection result of the abnormality in the lung sounds of each of the auscultation positions detected by the detection unit and the condition information representing weight of the patient.

Supplementary Note 3

The analysis device according to supplementary note 1 or 2, wherein the determination unit revises the severity determined based on the condition information, after determining the severity on the basis of the detection result of the abnormality in the lung sounds of each of the auscultation positions detected by the detection unite.

Supplementary Note 4

The analysis device according to any one of supplementary notes 1 to 3, wherein
the determination unit determines the severity according to a condition of the patient at a time of discharge from hospital, by referring to information created according to the condition of the patient at the time of discharge from the hospital.

Supplementary Note 5

The analysis device according to any one of supplementary notes 1 to 4, wherein
the decision unit decides the instruction on the basis of the result of the determination by the determination unit and the condition information representing the condition of the patient.

Supplementary Note 6

The analysis device according to any one of supplementary notes 1 to 5, wherein
the decision unit decides the instruction on the basis of the result of the determination by the determination unit and the condition information representing medication of the patient.

Supplementary Note 7

The analysis device according to any one of supplementary notes 1 to 6, wherein
the decision unit corrects the instruction decided based on the condition information after deciding the instruction on the basis of the result of the determination by the determination unit.

Supplementary Note 8

The analysis device according to any one of supplementary notes 1 to 7, wherein
the decision unit decides the instruction corresponding to a condition of the patient at a time of discharge from hospital by referring to information created according to the condition of the patient at the time of discharge from the hospital.

Supplementary Note 9

The analysis device according to any one of supplementary notes 1 to 8, wherein
the decision unit decides a medication instruction and a next examination instruction to the patient on the basis of the result of the determination by the determination unit.

Supplementary Note 10

The analysis device according to any one of supplementary notes 1 to 9, further comprising
an output unit that outputs the instruction decided by the decision unit.

Supplementary Note 11

The analysis device according to supplementary note 10, further comprising
an emergency report unit that provides an emergency report according to a state after the output of the instruction by the output unit.

Supplementary Note 12

The analysis device according to any one of supplementary notes 1 to 11, wherein
the condition information includes at least one of weight, medication, blood pressure, pulse, subjective symptoms, water intake, and percutaneous arterial blood oxygen saturation of the patient.

Supplementary Note 13

An analysis method comprising, by an information processing device:
detecting abnormality in lung sounds for each of auscultation positions on a basis of time-series acoustic signals including lung sounds of each of the auscultation positions;
determining severity of heart failure of a patient on a basis of a detection result of abnormality in the lung sounds of each of the auscultation positions detected and condition information representing a condition of the patient; and
deciding an instruction to be output to the patient on a basis of a result of the determination.

Supplementary Note 14

A computer-readable medium storing thereon a program for causing an information processing device to implement:
a detection unit that detects abnormality in lung sounds for each of auscultation positions on a basis of time-series acoustic signals including lung sounds of each of the auscultation positions;
a determination unit that determines severity of heart failure of a patient on a basis of a detection result of abnormality in the lung sounds of each of the auscultation positions detected by the detection unit and condition information representing a condition of the patient; and
a decision unit that decides an instruction to be output to the patient on a basis of a result of the determination by the determination unit.

REFERENCE SIGNS LIST 100 analysis device
110 electronic stethoscope
120 operation input unit
130 screen display unit
140 communication I/F unit
150 storage unit
151 lung sound data
152 analysis result information
153 severity determination information
154 severity information
155 instruction decision information
156 personal condition information
157 program
160 arithmetic processing unit

23

161 lung sound acquisition unit
162 abnormality detection unit
163 severity determination unit
164 instruction decision unit
165 output unit
166 emergency report unit
200 analysis system
210 analysis device
220 server device
230 network
300 analysis device
301 CPU
302 ROM
303 RAM
304 program group
305 storage device
306 drive
307 communication interface
308 input/output interface
309 bus
310 storage medium
311 communication network
321 detection unit
322 determination unit
323 decision unit

What is claimed is:

1. An analysis device comprising:
at least one memory configured to store instructions;
at least one processor configured to execute instructions to:
   detect abnormality in lung sounds for each of auscultation positions on a basis of time-series acoustic signals including lung sounds of each of the auscultation positions;
   determine, as a determination, a severity of heart failure of a patient on a basis of a detection result of abnormality in the lung sounds of each of the auscultation positions and condition information representing a condition of the patient; and
   decide an instruction to be output to the patient on a basis of a result of the determination;
an electronic stethoscope configured to acquire digital time-series acoustic signals including lung sounds from a plurality of predetermined auscultation positions on anterior and posterior chest regions;
a screen display unit;
a communication interface; and
a storage unit storing tables created in accordance with the condition of the patient, and the condition of the patient is the patient's condition at hospital discharge,
wherein the at least one processor is further configured to execute the instructions to:
   segment the digital time-series acoustic signals into inspiratory phases, expiratory phases, and pause phases by detecting breathing timing;
   suppress background noise in any of the inspiratory phases and the expiratory phases by subtracting a frequency-domain representation of a pause phase from a frequency-domain representation of the any of the inspiratory phases and the expiratory phases;
   for each of the auscultation positions, generate a time-frequency representation of the lung sounds and input the time-frequency representation into a trained abnormality-detection model to detect abnormal lung sounds;
   determine, as a determined severity, the heart-failure severity by referring to patient-specific severity determination information created in accordance with the condition of the patient at hospital discharge and that maps combinations of auscultation positions with detected abnormal lung sounds to severity classes;
   revise the determined severity based on personal condition information including at least weight and medication of the patient;
   decide, as a decided instruction, the instruction by referring to instruction decision information created in accordance with the patient's discharge condition, the instruction including at least one of a next-examination instruction, a medication instruction, and a seeking-diagnosis instruction;
   cause the screen display unit to output the decided instruction; and
   via the communication interface, transmit at least one of lung sound data, analysis results, severity, and the decided instruction to an external device, when a transmission condition is satisfied, and issue an emergency report when a reporting condition related to the decided instruction is satisfied.

2. The analysis device according to claim 1, wherein detecting the breathing timing includes estimating phase probabilities using a machine-learned model trained with time-series lung-sound signals.

3. The analysis device according to claim 1, wherein suppressing the background noise includes applying a band-pass filter adapted to a lung-sound frequency range.

4. The analysis device according to claim 1, wherein the trained abnormality-detection model comprises a convolutional neural network or a recurrent neural network receiving a spectrogram or a mel-frequency cepstral-coefficient feature map.

5. The analysis device according to claim 1, wherein the decision making for the instruction to be output to the patient is performed by referring to instruction decision information created in accordance with the patient's condition at hospital discharge and to the personal condition information.

6. The analysis device according to claim 1, wherein the decision making is revised when medication information in the personal condition information indicates a predetermined medication taken according to a predetermined schedule while the severity worsens.

7. The analysis device according to claim 1, wherein guidance for the predetermined auscultation positions is displayed to an operator and a quality index of the lung sounds is calculated, and when the quality index indicates insufficient quality, a warning is output and reacquisition is prompted.

8. The analysis device according to claim 1, wherein the transmission condition is satisfied when the severity meets a preset transmission policy, and the reporting condition is satisfied when the patient fails to follow the decided instruction within a predefined period.

9. The analysis device according to claim 1, wherein the external device includes a physician terminal configured to receive the transmitted information.

10. The analysis device according to claim 1, wherein the analysis device is part of a server-assisted analysis system in which at least part of abnormality detection, severity determination, instruction decision, or emergency reporting is executed by a server device communicatively connected to the analysis device.

11. The analysis device according to claim 1, wherein the condition information includes at least one of weight, medication, blood pressure, pulse, subjective symptoms, water intake, and percutaneous arterial blood oxygen saturation of the patient.

* * * * *